United States Patent
Davey et al.

(10) Patent No.: US 6,500,110 B1
(45) Date of Patent: *Dec. 31, 2002

(54) MAGNETIC NERVE STIMULATION SEAT DEVICE

(75) Inventors: Kent R. Davey, New Smyrna Beach, FL (US); Charles M. Epstein, Atlanta, GA (US)

(73) Assignee: Neotonus, Inc., Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/501,245

(22) Filed: Feb. 10, 2000

Related U.S. Application Data

(63) Continuation-in-part of application No. 09/125,646, filed on Mar. 15, 1999, now Pat. No. 6,132,361, which is a continuation of application No. 09/001,782, filed on Dec. 31, 1997, now Pat. No. 6,086,525, which is a continuation-in-part of application No. 08/345,572, filed as application No. PCT/US97/14826 on Aug. 15, 1997, now Pat. No. 5,725,471.
(60) Provisional application No. 60/023,421, filed on Aug. 15, 1996.

(51) Int. Cl.[7] .................................................. A61N 1/00
(52) U.S. Cl. ..................... 600/13; 600/29; 128/DIG. 25
(58) Field of Search ........................... 600/9–15, 29–32; 607/48–52; 128/DIG. 25

(56) References Cited

U.S. PATENT DOCUMENTS

| 5,197,940 A | * | 3/1993 | Sievert et al. ................. 600/13 |
| 5,725,471 A | * | 3/1998 | Davey et al. .................. 600/13 |
| 5,817,000 A | * | 10/1998 | Souder ......................... 600/15 |
| 6,042,531 A | * | 3/2000 | Holcomb ....................... 600/15 |
| 6,086,525 A | * | 7/2000 | Davey et al. .................. 600/13 |
| 6,179,769 B1 | * | 1/2001 | Ishikawa et al. .............. 600/15 |
| 6,223,750 B1 | * | 5/2001 | Ishikawa et al. .............. 600/13 |

* cited by examiner

Primary Examiner—John P. Lacyk
(74) Attorney, Agent, or Firm—Levisohn, Lerner, Berger & Langsam, LLP

(57) ABSTRACT

A magnetic nerve stimulator system is comprised of a core constructed from a material having a high field saturation with a coil winding. A thyrister capacitive discharge circuit pulses the device. A rapidly changing magnetic field is guided by the core, preferably vanadium permendur. For task specific excitation of various nerve groups, specially constructed cores allow for excitation of nerves at deeper levels with higher efficiency than is possible with air-core stimulators. Among the applications possible with this invention are treatment of incontinence, rehabilitation of large muscle groups in the leg and arm, and excitation of abdominal wall muscle groups to aid in weight loss and metabolic rate increase. A C-shape is employed for focussing the stimulation as desired.

34 Claims, 4 Drawing Sheets

MAGNETIC NERVE STIMULATION SEAT DEVICE

RELATED APPLICATIONS

The present application is a continuation of U.S. patent application Ser. No. 09/001,782 filed Dec. 31, 1997, now U.S. Pat. No. 6,086,525, which is a continuation-in-part of U.S. patent application Ser. No. 08/345,572, filed Nov. 28, 1994 (patented and issued as U.S. Pat. No. 5,725,471). The present application is also a continuation-in-part of U.S. patent application Ser. No. 09/125,646 filed Mar. 15, 1999, now U.S. Pat. No. 6,132,361, which claims priority to PCT Application Ser. No. PCT/US97/14826 filed Aug. 15, 1997, which claims priority to U.S. Provisional Application Ser. No. 60/023,421 filed Aug. 15, 1996. All rights of priority are claimed to those prior applications, the disclosures of which are fully incorporated herein by reference.

BACKGROUND OF THE INVENTION AND DESCRIPTION OF THE PRIOR ART

A nerve cell can be excited in a number of different ways, but one direct method is to increase the electrical charge within the nerve, thus increasing the membrane potential inside the nerve with respect to the surrounding extracellular fluid. One class of devices that falls under the umbrella of Functional Electrical Stimulation (FES) realizes the excitation of the nerves by directly injecting charges into the nerves via electrodes which are either placed on the skin or in vivo next to the nerve group of interest. The electric fields necessary for the charge transfer are simply impressed via the wires of the electrodes.

FES is accomplished through a mechanism which involves a half-cell reaction. Electrons flow in wires and ions flow in the body. At the electro-electrolytic interface, a half-cell reaction occurs to accomplish the electron-ion interchange. Unless this half-cell reaction is maintained in the reversible regime, necrosis will result—partially because of the oxidation of the half-cell reaction and partially because of the chemical imbalance accompanied by it.

The advantage of FES is that the stimulation can usually be accomplished from extremely small electrodes with very modest current and voltage levels. The disadvantage however, is that it involves half-cell reactions. Most rehabilitation programs using FES place the electrodes directly on the skin. A conductive gel or buffering solution must be in place between the electrodes and the skin surface. Long term excitation of nerve or muscle tissue is often accompanied by skin irritation due to the current concentration at the electrode/skin interface. This problem is especially aggravated when larger excitation levels are required for more complete stimulation or recruitment of the nerve group.

By contrast, magnetic stimulation realizes the electric fields necessary for the charge transfer by induction. Rapidly changing magnetic fields induce electric fields in the biological tissue; when properly oriented, and when the proper magnitude is achieved, the magnetically induced electric field accomplishes the same result as realized by FES, that of transferring charge directly into the nerve to be excited. When the localized membrane potential inside the nerve rises with respect to its normal negative ambient level of approximately −90 millivolts (this level being sensitive to the type of nerve and local pH of the surrounding tissue), the nerve "fires."

The present invention is especially targeted at applications that are not suited for the use of implanted electrodes. The invention is designed for non-invasive external stimulation of selected nerve or nerve groups, particularly in certain applications. In these applications, which include incontinence and rehabilitation of muscle groups as well as potential weight loss treatment, the desired excitation levels using FES often fall outside of what might be considered comfortable limits. That is, the electrical current that ideally would be injected through the skin to excite the muscle groups of interest often leads to some skin irritation with time. The invention can also be used even in applications where this is not the case, as the use of gels and direct electrode/skin placement is inconvenient and is often resisted by the patient.

As opposed to FES, magnetic excitation has the attractive feature of not requiring electrode skin contact. Thus, stimulation can be achieved through the clothing that is being worn. This overcomes the objection of inconvenience and preserves the patient's dignity. Secondly, because there is no direct contact, stronger excitation levels can be realized without undue additional skin irritation. A contribution offered by the present invention is the ability to achieve higher levels of focusing of the magnetic field and thus stimulation within the patient. Commensurate with this greater level of focusing comes some flexibility in the number of possible applications that might be targeted. Also accompanying the focusing is a higher level of power efficiency. Typically, the devices being designed by the methods outlined in this invention reduce the magnetic reluctance path by a factor of two. This reluctance reduction translates into a diminution of the current by the same factor and a fourfold reduction in power loss.

Magnetic stimulation of neurons has been heavily investigated over the last decade. Almost all magnetic stimulation work has been done in vivo. The bulk of the magnetic stimulation work has been in the area of brain stimulation. Cohen has been a rather large contributor to this field of research (See e.g., T. Kujirai, M. Sato, J. Rothwell, and L. G. Cohen, "The Effects of Transcranial Magnetic Stimulation on Median Nerve Somatosensory Evoked Potentials", *Journal of Clinical Neurophysiology and Electro Encephalography*, Vol. 89, No. 4, 1993, pps. 227–234.) This work has been accompanied by various other research efforts including that of Davey, et al. (See, K. R. Davey, C. H. Cheng, C. M. Epstein "An Alloy-Core Electromagnet for Transcranial Brain Stimulation", *Journal of Clinical Neurophysiology*, Volume 6, Number 4, 1989, p.354); and that of Epstein, et al. (See, Charles Epstein, Daniel Schwartzberg, Kent Davey, and David Sudderth, "Localizing the Site of Magnetic Brain Stimulation in Humans", *Neurology*, Volume 40, April 1990, pps. 666–670). The bulk of all magnetic stimulation research attempts to fire nerves in the central nervous system.

The present invention differs in a number of respects from previous research efforts. First, the present invention has primary applicability to the peripheral nervous system, although it can be employed to stimulate nerves in the central nervous system as well. Second, and more importantly, the previous nerve stimulation work is dominated almost exclusively by air core coils of various shapes and sizes. The present invention is directed to the use of a magnetic core, more specifically a permeable core having a high field saturation, with the most preferred material being vanadium permendur. Among the air core stimulators are circles, ovals, figure eights, and D shaped coils. The coils are normally excited by a capacitive discharge into the winding of the core of these coils. This exponentially decaying field has a time constant typically in the neighborhood of 100 microseconds. Typical target values for the magnetic field peak happen to be near two Tesla. J. A. Cadwell is perhaps the leader among those who are now using and marketing these air core stimulators. Among his primary patents is U.S. Pat No. 4,940,453 entitled "Method and Apparatus for Magnetically Stimulating Neurons" Jul. 10, 1990. There are a number of power supplies all of which operate on a basic capacitive type discharge into a number of air core coils which are sold with his units. Various shaped coils are being explored at this time. One such coil is a cap shaped device which fits over the motor cortex (K. Krus, L. Gugino, W. Levy, J. Cadwell, and B. Roth "The use of a cap shaped coil for transcranial stimulation of the motor cortex", *Journal of Neurophysiology*, Volume 10, Number 3, 1993, pages 353–362).

Some efforts are being given to various circuits used to fire these air core coils. H. Eton and R. Fisher offer one such alternative in their patent "Magnetic Nerve Stimulator" U.S. Pat. No. 5,066,272 Nov. 19, 1991. They suggest the use of two capacitors—one to capacitively discharge into the coil of interest, and a second to recover the charge from the inductive energy resident in the coil. The circuit used in the present invention accomplishes the same objective with a single capacitor.

Some stimulation research is being performed on the peripheral nervous system (See e.g., Paul Maccabee, V. Amassian, L. Eberle, and R. Cracco, "Magnetic Coil Stimulation of Straight and Bent Amphibian and Mammalian Peripheral Nerve in vitro: Locus of Excitation," *Journal of Physiology*, Volume 460, January 1993, pages 201–219.) The bulk of Maccabee's work is however targeted for cranial excitation. The applications of the present invention focus on the peripheral nervous system although it can be used on the central nervous system, as well.

SUMMARY OF THE INVENTION

An object of the present invention is to provide a magnetic nerve stimulator for exciting nerves of the peripheral nervous system.

A further object of the present invention is to provide a magnetic nerve stimulator for non-invasive stimulation of nerves within the peripheral nervous system.

A further object of the present invention is to provide a nerve stimulator for the production of magnetic fields of significant depth and focusability to stimulate deep nerves within a human.

A further object of the present invention is to provide a magnetic nerve stimulator which can produce magnetic fields which can be focused on internal peripheral nerves to effect non-invasive nerve stimulation.

A further object of the present invention is to provide a magnetic nerve stimulator for the treatment of bladder and urinary disorders.

A further object of the present invention is to provide magnetic nerve stimulators for the treatment of incontinence.

A further object of the present invention is to provide a magnetic nerve stimulator for muscle rehabilitation and/or conditioning.

A further object of the present invention is to provide a magnetic nerve stimulator for use in assisting with weight loss.

Further objects of the invention will become apparent in connection with the disclosure provided herein.

To accomplish the objectives of the present invention, a magnetic nerve stimulator is provided herein which can be used to stimulate nerves without the need for surgery. Magnetic stimulation of peripheral nerves has the advantages of convenience and threshold variability over competing FES systems. An advance of the present invention over competing magnetic nerve stimulators is in the use of a highly saturable magnetic core, i.e. a permeable core of high field saturation, and in the design of the magnetic core stimulator itself.

In the preferred embodiment, the magnetic nerve stimulator is preferably constructed using a core of a magnetic or magnetizable material. A permeable material having a high field saturation is utilized, with the preferred core having a field saturation of at least 1.5 Tesla. Some suitable materials for the core include vanadium permendur, orthinol, metallic glasses (metglass), permalloy, supermalloy, powdered iron, and the silicon irons or silicon steels, in particular, 3% grain oriented steel (magnesil). Ferrite can also be used, although it is not preferred, due to the fact that it saturates at 0.5 T.

In accordance with the present invention, it is highly preferred that an open core be used. Toroidal cores are not preferred, as it is has been found that an open core can be more effectively utilized to focus the magnetic field produced by the stimulator, and as the suitability of toroidal cores have been found to be limited to invasive applications. By the term open core, an arc shaped core spanning an angle less than 360 degrees is intended. A 180 degree core is very convenient for using the material efficiently since two cores can be constructed from every mandrel. A core having a larger angle (e.g. 210–220 degrees) can also be used. These cores are more focussed, although they have a smaller penetration depth. Alternatively, cores of smaller or greater angles can be used in non-preferred embodiments.

In the current embodiments of the invention, it is an objective to "fire" a coil having approximately a 100 microsecond characteristic decay time, five (5) to fifty (50) times per second. The system must be reasonably efficient and reliable to fire at such a high repetition rate. Firing rates of 5 to 10 Hz are known to be effective for treating urinary stress incontinence using FES. Higher stimulation rates (e.g. fifty (50) Hz) have proved useful for treating irritative symptoms of urinary frequency and urgency. Sustained contractions occur above fifteen (15) Hz. As medical knowledge advances, various and as further research is conducted, other firing rates of higher or lower frequencies, or of particular excitation patterns, may prove useful in specific applications.

The exact stimulation frequency will be varied somewhat depending on the requirements of the application in need. Sometimes muscle groups will need to be excited for a five second period, followed by rest for a five second period and then be stimulated continuously for another five seconds and then rest again. While they are being stimulated, it is often desirable to have the muscle groups in a sustained contraction. This requirement dictates the necessity of continuing to pulse the cores at a repetition rate of 15 Hz. Because of the large currents involved during any given firing of the core, it is necessary to make the cores as efficient as possible. It is desirable to focus the magnetic field into the region targeted for stimulus to the exclusion of surrounding regions. The specially designed cores offered by this invention realize that focusability, whereas the air core coils used by the prior art do not.

With respect to the core configuration, the simplest core configuration of the present invention is that of a "C" shaped core. The span of the "C" must be carefully chosen; the span affects both the penetration depth and the magnitude of the field. Of additional importance is the construction of the core. The best cores are constructed from thin laminate materials having a high field saturation. A typical core can be wound using two mil stock of vanadium permendur. A long ribbon of such material is wound on a mandrel (e.g. a mandrel of wood or plastic) for the radius, thickness and depth desired. Each side of the ribbon is coated with a thin insulative coating to electrically isolate it from its neighbor. A generic core that might be used at various locations around the body can span an angle of approximately 180–220°. Once the ribbon has been wound on the mandrel to the desired dimensions, it is dipped in epoxy to freeze its position. Once the epoxy has cured, the mandrel is removed and the core cut for the span of angle desired. The cut will destroy the electrical isolation of adjacent laminations. Each cut must be finely ground so that it is smooth, and then a deep etch performed. The deep etch is performed by dipping each of the cut ends in an acid bath. This causes the cut ends to delaminate slightly, but maintains the electrical isolation of the laminations. Failure to perform this deep etch results in considerable eddy current loss and heating at the cut ends of the core. Following the deep etch, the ends are brushed with epoxy to maintain the shape and structural integrity of the core. The final step of the construction is to wind a coil of insulated wire about the core. A typical inductance for a core of this type is about 30 $\mu$H. The present invention, however, may be practiced at other inductances or magnetic field strengths, as well.

In the simplest configuration, each core has only one winding. The winding is excited by an exponentially decaying pulse with a characteristic time of about 100 $\mu$s. The actual signal has a ringing period of about that time within an envelope that is exponentially decaying so that only two to three cycles are ever witnessed by the coil current. The excitation is repeated on a period of about approximately 5–50 Hz. As stated above, the repetition cycle of these patterns will be varied according to the application. The circuit usually consists of a transformer which feeds into a full wave rectifier bridge. The bridge voltage charges the capacitor; the charge on the capacitor is triggered with a silicon control rectifier to drive current into the coil. The return charge coming back through the coil the second time is fed through the diode back into the capacitor to prepare the circuit for the second phase of excitation.

There are at least three important target applications for the present invention—incontinence, muscle rehabilitation, and weight control treatment. For the treatment of incontinence, it is necessary to stimulate the pelvic floor muscles. Such a stimulation is achieved by concentrating and focusing magnetic flux directly up the vaginal cavity. One suitable core which is capable of realizing this objective is constructed by combining two individual "C" cores each spanning an angle of about 180°. The legs of the cores are brought together in a central region. The common central leg of the two "C" cores is wound by a coil and the return path for the flux is split between the two "C"s. The cores themselves fit proximally and distally under a chair which the patient sits on during treatment.

A second area of application is in the rehabilitation of muscles. The primary muscle groups targeted are the thigh, calf, biceps, and triceps. The geometry is similar for all these applications, and thus a cylindrical extension around the muscle is used. Although one solution for this problem is a simple "C" core and coil which is moved around by the discretion of the patient, an alternative stimulator resembles the tubular shape motors used in electromechanics to propel a secondary member down a tube. Here the geometry would necessarily require a hinged tubular shape having recesses or slots which would run azimuthally around the muscle group to be stimulated. The coils of the stimulator fits in these recesses or slots and the surrounding structure would again be a laminated vanadium composite. If the structure were fitted with two or three coils, they could be stimulated in a phased arrangement.

Such an excitation would have the effect of kneading the muscle tissue group along its longitudinal axis. This particular excitation pattern may be instrumental in more fully recruiting larger muscle groups such as the hamstring group in the leg. Full recruitment or stimulation of the nerve group would be advantageous to long term rehabilitation. Preliminary experiments with the device indicate that excitations at the frequencies mentioned accomplish exercise of the muscles at a higher efficiency and rate than could be accomplished through normal means.

Another area of application is that of assisting in weight loss management. As with muscle rehabilitation, one alternative is to simply use a handheld unit moved over multiple areas of the body. One group which can be particularly difficult to stimulate is the abdominal wall. An alternative method for realizing excitation of this group resembles a chest plate which can be secured to a patient or hinged to the side of a chair in which the patient sits. The chest plate contains a two or three phase arrangement of coils backed by the high field saturation cores constructed in the manner dictated above. The cores are spaced to drive the flux deeply within the abdominal muscle group. Both in muscle rehabilitation and in weight loss management, the phasing of the coils can be alternated with time to give the effect of a back and forth "kneading" stimulation pattern. The rationale behind weight management is that the firing of these muscle groups requires the uptake of adenosine triphosphate; this energy expenditure is being artificially induced by the magnetic stimulator.

In summary, it is noted that there are a number of ways to more efficiently stimulate various muscle groups within the body. The key to these more efficient techniques revolves around using a thin laminate material of high magnetic field saturation to construct these cores and thereby drive and focus the flux into the regions desired. A simple "C" type core achieves a reluctance advantage of at least a factor of two over conventional cores. By using multiple cores connected at a center leg, a single focus site can be achieved with the return path disbursed in two or more areas so as to discourage excitation when the field is returned. In other applications, multiphased coils that actually enclose the tissue of interest can be excited so as to roll or knead muscle groups directionally with time. Certain wrapping applications may be more instrumental for higher recruitment of injured muscle groups.

DETAILED DESCRIPTION OF THE INVENTION AND THE PREFERRED EMBODIMENTS

Figure 1:
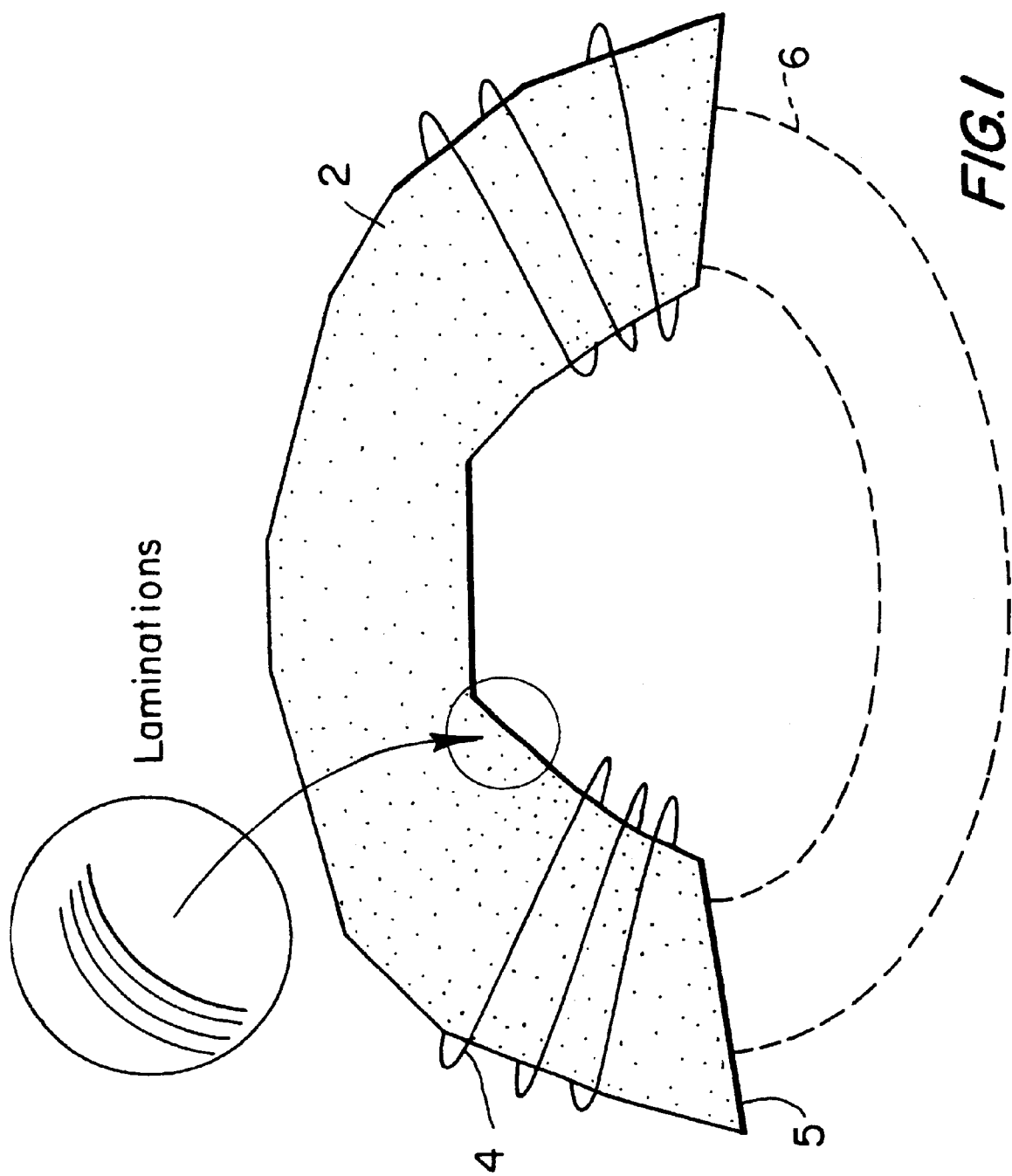
FIG. 1 is a plan view of a "C" shaped core stimulator with the toroidal coil field winding wrapped around the core. The field lines (dotted) indicate the depth of penetration and focusing of the stimulation.

In accordance with the present invention, a magnetic nerve stimulator is provided which can be used for non-invasive stimulation of nerves in the peripheral nervous system. The advantage of non-invasive stimulation is a significant one, as nerves can be stimulated deep beneath the surface of the skin without the necessity for surgery, incisions in the body, or the use of uncomfortable electrodes. To achieve an effective non-invasive stimulator, however, the stimulator must be carefully designed to achieve sufficient depth and penetration within the body so as to effectively stimulate the nerves or nerve groups of interest.

The present inventors have recognized the objective of highly effective non-invasive stimulation by providing a magnetic nerve stimulator which can achieve significant depth and penetration, such that internal human nerve groups can be stimulated to treat incontinence, achieve muscle rehabilitation (or conditioning) or assist with weight loss.

In the preferred embodiment, the core is constructed out of a permeable magnetic material having a high field saturation. By high field saturation, the inventors refer to the fact that a magnetizable material is utilized which saturates at 1.5 Tesla or higher.

The magnetic nerve stimulator is preferably made with a magnetizable material. Since the magnetic fields desired typically reach 1.5 Tesla or higher, it is desirable to use materials which saturate at or above 1.5 Tesla. One suitable material, for example, is vanadium permendur. Other suitable materials include the metallic glasses (i.e. metglass), permalloy, supermalloy, powdered iron, and silicon irons or silicon steels, in particular, 3% grain oriented steel (magnesil). Ferrite can also be used, although it is not preferred, due to the fact that its saturates at 0.5 T. These materials can be obtained, for example, from Magnetics, Inc. in Butler, Pa.

It has been found that 3% grain oriented silicon steel is a particularly useful core material. This material has the advantage of providing very good performance at a relatively low cost. Grain oriented steel is also useful since it can be wound on a bobbin. A higher field can be reached when the magnetic grains are oriented azimuthally (around the bobbin) in the direction that the field will travel.

A summary of some materials which can be used for the core and their characteristic properties is as follows:

TABLE I

Materials for the Magnetic Core

| Material | Frequency | Saturation |
| --- | --- | --- |
| Permendur | <5 kHz | 2.2 T |
| Magnesil (3% grain oriented steel) | <1 kHz | 1.75 T |
| Powdered iron | <10 kHz | 1.75 T |
| Metglass | <100 kHz | 1.5 T |
| Orthinol | <10 kHz | 1.45 T |
| Permalloy | >10 kHz | 0.7 T |
| Supermalloy | >10 kHz | 0.7 T |
| Ferrite | <500 kHz | 0.5 T |

Thus, in general, the use of a magnetizable material is preferred for the core as it helps to focus and enhance the magnetic field used for nerve stimulation. Accordingly, materials with a high field saturation, i.e. materials saturating at 1.5 Tesla or higher, are recommended. With some materials, a saturation of 2.0 Tesla can be achieved. Although, in accordance with the disclosure herein, magnetic nerve stimulators can also be constructed using materials which saturate at lower fields, for example, materials which saturate at 1.0 Tesla or higher, or even at 0.5 Tesla or higher, such as ferrite. These stimulators are not preferred, however, as they have been found to be less effective.

In accordance with the present invention, the use of an open core is desirable as well. By the term "open core", the inventors refer to the fact that the core is curved into an arc such that there is a gap or opening between the ends of the core. This enables the magnetic field generated by the core to be more strongly and precisely focussed beyond the opening and therefore, beneath the surface of the skin. Thus, an open core is used to provide a desirable degree of penetration and focussing and thereby improve the stimulator's effectiveness.

The open core is non-toroidal, i.e. it spans an arc of less than 360 degrees, with a gap between the ends of the core. In the preferred embodiments, the open core is C-shaped. A preferred angle for the span of the arc of the core is approximately 180–220 degrees. In the preferred embodiments, a suitable core can span an angle from approximately 205 to approximately 215 or 220 degrees. In other embodiments, cores of approximately 190–230 degrees can be utilized. Alternatively, a core spanning an arc of approximately 180–270 degrees are also possible. The greater the arc angle, the better the field focussing, however, the penetration depth is lower. Unless the geometry demands it, there is believed to be no advantage to a core spanning an angle less than 180 degrees.

A large radius is also recommended for the core to stimulate deep nerves. The magnetic field falls off exponentially as the inverse distance between the pole heads. A small radius core has a very high field between the heads, but the field falls off rapidly. A large core has a lower field between the heads, but the field falls off less rapidly. Thus, the larger radius core will have a higher field a few centimeters into the body. For incontinence treatment, it is desired to stimulate the pelvic floor muscles. A penetration depth of at least 5 cm for this task is recommended, and thus a larger radius core is preferred. Placing two (2) cores together has the advantage of concentrating the field in one point. The field is cut in half at the return points. This discourages secondary stimulation sites. For a handheld device, an outer diameter of approximately 5" and an inner diameter of approximately 4" is recommended. For the incontinence device, an outer diameter of approximately 6" and an inner diameter of approximately 3" is recommended. For the coil, 15 kVolt No. 6 AWG wire with 15 kV insulation can be utilized.

The present device yields much greater stimulus for the same current as prior art devices, which is a significant improvement in performance. One test of the device, for example, demonstrated nearly twice the stimulus over a well known prior art device, for the same amount of current.

Another important advantage of the present invention is that the design of the stimulator allows magnetic treatment to be external. By "external", the present inventors refer to the fact that stimulation can be achieved without implantation of any elements within the body, or engaging in any surgery or surgical incision. Thus the use of an internal element of any sort in the human body, such as, for example, an implanted electrode, is not necessary. The high field saturation material used in the stimulator provides a magnetic field of sufficient depth and focusability to effectively penetrate the organism and stimulate the internal nerves within the organism without the need for any invasive surgery. This is a particularly great advantage in the treatment of incontinence. It is also of potential usefulness in other applications as well.

As shown in FIG. 1, a "C" shaped core is disclosed which is capable of stimulating various peripheral nerve groups throughout the body. The core 2 is constructed by winding two to four mil laminations of a material having a high magnetic field saturation on a mandrel; the number of laminations required will be dictated by the thickness and depth of the core desired.

This closed loop spool of laminations is removed from the mandrel and coated with epoxy to give the unit structural integrity. The closed loop is then cut to give the length and angle of the "C" shape, as desired. A deep acid etch is then performed on the cut edges. The cut edges are soaked in an acid bath which causes the epoxy to dissolve resulting in a slight delamination of the core in the vicinity of the cut. Epoxy is then brushed on the etched ends to prevent further delamination. This procedure is necessary to prevent eddy currents from flowing in the core. This would diminish the effective B field which can be produced by the core.

The laminate material should be constructed of a saturable material, and preferably a material having a high field saturation. As previously described, the characteristic magnetic fields in the cores have preferred strengths of at least 1.5 Tesla. With suitable materials, characteristic fields in the range of at least two Tesla can be achieved. Preferably, vanadium permendur or 3% grain oriented steel is used, as these materials carry a high field density, although the present invention is not limited to those preferred embodiments. In the present stimulators, high field saturation is more important than high permeability.

In addition to the factor of high saturation, it can also be desirable in preferred embodiments to choose the core to minimize heat production and/or to minimize noise levels. In particular, minimization of hysteresis losses is desirable. Hysteresis is internal loss due to a change of orientation of the molecular structure of the core material. This is related to how open the BH loop is. Hysteresis is probably the chief contributor to the heating in the core. When an applied field changes the length of the material, the material is referred to as displaying magnetorestriction. This can result in noise during the stimulator's operation. Eddy current losses can be addressed by using small thickness stock or even powder.

One useful material to achieve low hysteresis losses and low magnetorestriction are the supermalloy products. These materials have a high nickel content (50%–80%). The 80% nickel variation has very low hysteresis losses, although the material saturates at only 0.7 T. These nickel alloys can be obtained in half mil thicknesses.

Another material which can be used is metglass. This is a metalized iron-glass material with low internal resistance. The normal material has a trade name of NAMGLASS1 or SA1. This material can be transverse field annealed. This process orients the grain structure at right angles to the field flow use. The annealing lowers the hysteresis loss significantly. It also lowers the permeability, although that effect is not of significance for the purposes of the present stimulator. The material also has very low magnetorestriction.

Another material, pure iron, is very soft and has a rounded loop. This ductility is believed to reduce the noise. It saturates at 1.7 T and is often found in powdered cores.

As noted above, another useful material for the core, in general, is 3% grain oriented steel. A generic name for this material, which is used by some manufacturers, is magnesil. The material is essentially steel with 3% silicone, and saturates at 1.75 T. Another suitable material for the core is supermendur. This material includes iron and cobalt and saturates at 2.2 T. Both of these materials, however, are highly magnetostrictive, changing length when exposed to a magnetic field. Both materials also have a square BH loop.

After choice of the core, a winding or coil 4 is then wrapped around the core in such a way as to drive the flux through the cut ends 5. The field lines 6 give an indication of the depth of penetration and degree of focusing expected with such a core.

Figure 2:
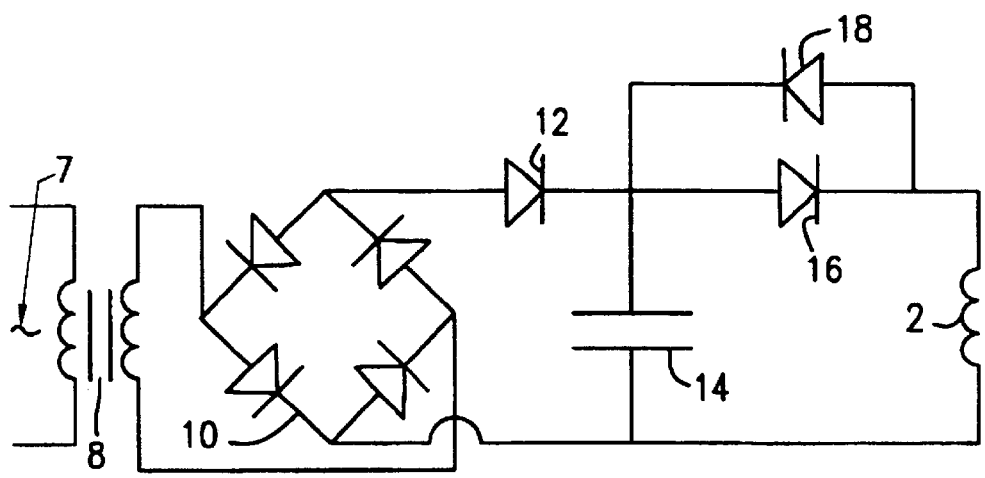
FIG. 2 is a schematic of the electrical circuit used to stimulate the coil winding.

FIG. 2 shows an electrical circuit used to "fire" the core and coil of FIG. 1. A normal 120 volt, 60 Hz signal excites the circuit at 7. A transformer 8 amplifies the voltage up to about 1–3 kV. This high voltage AC signal is then fed into a full wave rectifier bridge 10. The signal from the rectifier bridge is then passed through a diode 12 to charge a capacitor 14. The purpose of all the electrical components to the left or upstream of the capacitor is to simply put charge into the capacitor. The energy residing in the circuit which will be pumped into the stimulator core is one-half C (the capacitance value) times the voltage squared. When thyristor 16 is triggered with a small control voltage pulse, current flows through the thyristor and into the core 2. Most of this energy goes back into the capacitor 14, recharging it in the opposite polarity from its initial charge. The reverse charged capacitor 14 immediately discharges again through the stimulator coil 2 through diode 18, connected in parallel. Theoretically, all of this energy should pass into capacitor 14 to recharge it according to its initial polarity. In practice, of course, this LC circuit has some loss, and the thyristor 16 does not shutoff immediately. Two to three exponentially decaying ring cycles of this L circuit are witnessed in practice before current of core 2 is completely shut off. After shutoff, the capacitor charges through diode 12 as it did initially. It continues to charge until thyristor 16 is triggered again.

Different stimulation/rest cycles are employed for different tasks. In the treatment of incontinence, one such stimulation cycle might be five seconds on, five seconds off. During the five seconds which are characterized as "on", thyristor 16 could continuously be pulsed 15 times per second. These stimulation montages can be altered according to the requirements and goal of the stimulation protocol.

The circuit shown is a preferred embodiment for the practice of this invention but other circuit designs (such as a dual capacitor arrangement or so forth) may be used to fire the coil as well, as will be apparent to those skilled in the art. Moreover, whereas the magnetic field produced by this embodiment pulses at approximately 20–50 kHz, variations in that frequency may be practiced as well. This frequency is simply:

$$1/2\pi\sqrt{LC} \quad \text{(Equation 1)}$$

Figure 3:
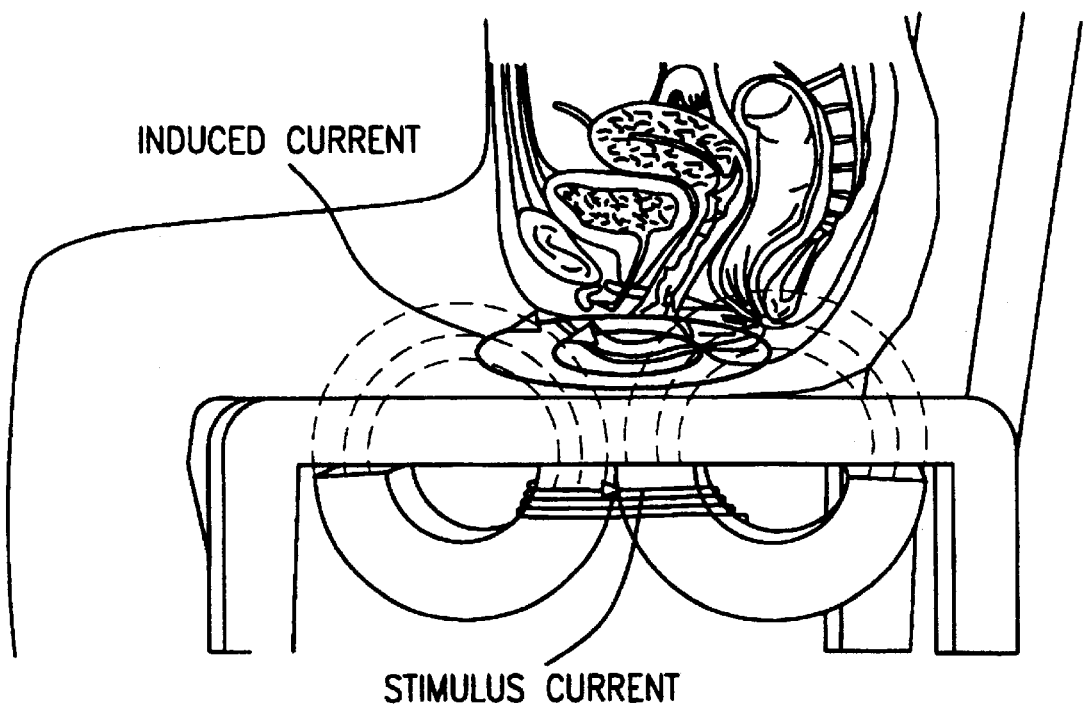
FIG. 3 is a side view of a core stimulator configuration used in the treatment of incontinence; the core is designed to fit underneath a seat which the patient sits on during treatments.

Shown in FIG. 3 is a dual "C" core type arrangement suitable for the treatment of incontinence. The individual "C"s comprising this core each span an angle of about 220°. The cores 20 are placed end to end in a W type arrangement. The winding 4 is wrapped around the common center leg of the two cores. The cut ends of these cores are designed to be flush with the lower side of a saddle cushion 21 in which the patient sits. The primary flux is driven up the common central core into the vaginal cavity. This flux is returned through the posterior and anterior arms of the "W". Because the return flux is much lower in magnitude, no stimulation occurs except at the vaginal floor near the center leg of the "W".

Figure 4:
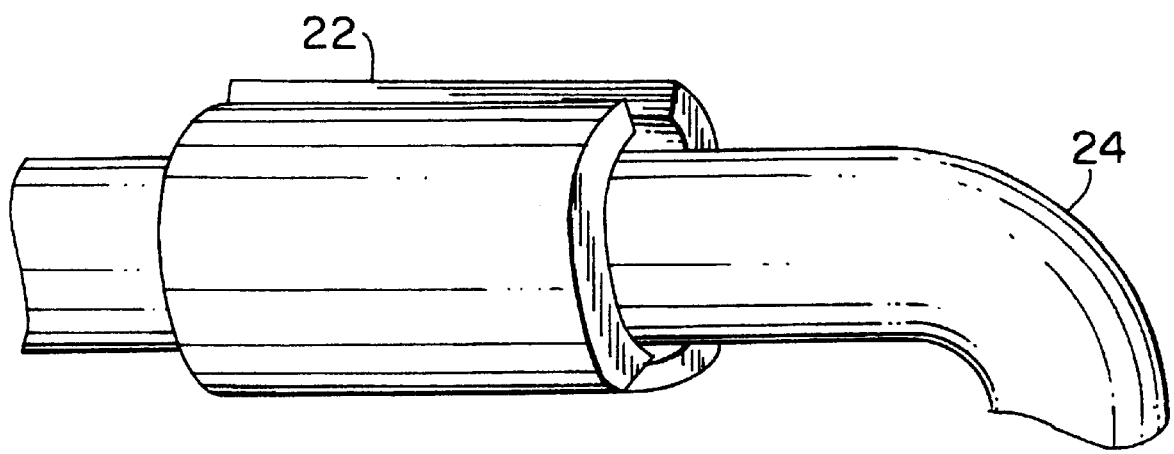
FIG. 4 is a perspective view of a core stimulator (wrapped around a patient's leg) used to massage muscles in the leg for rehabilitation purposes. The tubular core is hinged on one side and is designed to fold around the leg.
Figure 5:
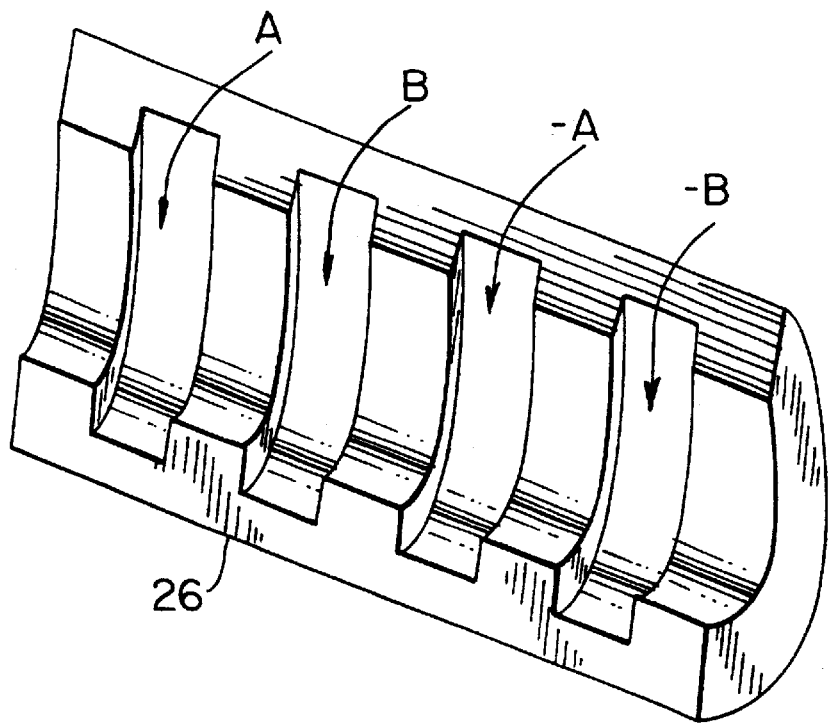
FIG. 5 is a perspective view of a half section of the core stimulator used for arm or leg muscle rehabilitation; windings of different phases are placed in adjacent recesses or slots, cut into the core.
Figure 6:
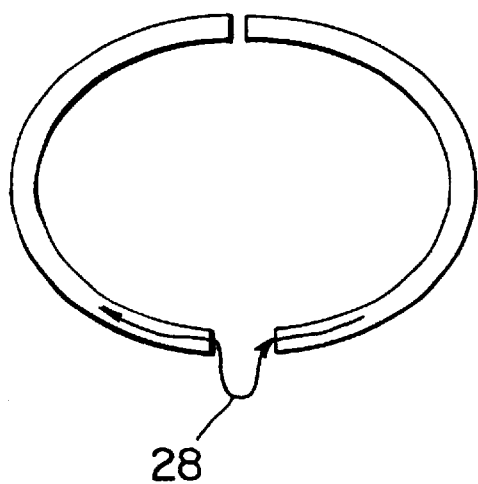
FIG. 6 is an end view of the leg or arm stimulator. The winding going from one section to the next is taken out in a long fold to allow for ease of opening of the core units for facilitating placement around the leg or arm.

FIG. 4 shows a core stimulator suitable for exciting leg and arm muscle groups. In this configuration the cores 22 would constitute a tubular type shroud into which a leg 24 or an arm would be inserted. Although the "C" core of FIG. 1 would be suitable for this task, its geometry is difficult to achieve a homogenous and controlled stimulus of this muscle group. As shown in FIG. 5, each section of the stimulator 22 is comprised of two half shells 26. Recesses or slots 27 are cut into the half shells to allow placement of coils which will be wound preferentially within the shells. The individual windings of the shell 26 are aligned in such a way as to create a magnetic field which is preferentially along the axis of the arm or the leg. Adjacent recesses or slots of the stimulator 22 will contain different phases. A two or three phase arrangement is used to excite a traveling magnetic field which moves down and up the axis of the arm/leg. This winding arrangement is not unlike that used in tubular motors to realize an axial traveling wave. One edge of the two common halves constituting the stimulator 22 must act as a hinge. The winding electrically connecting the two halves is simply accomplished by bringing the wire down as an extension 28 as suggested in FIG. 6. The extra length of winding associated with the extension 28 guarantees the needed flexibility of the stimulator to hinge and wrap around the patient's arm or leg.

Figure 7:
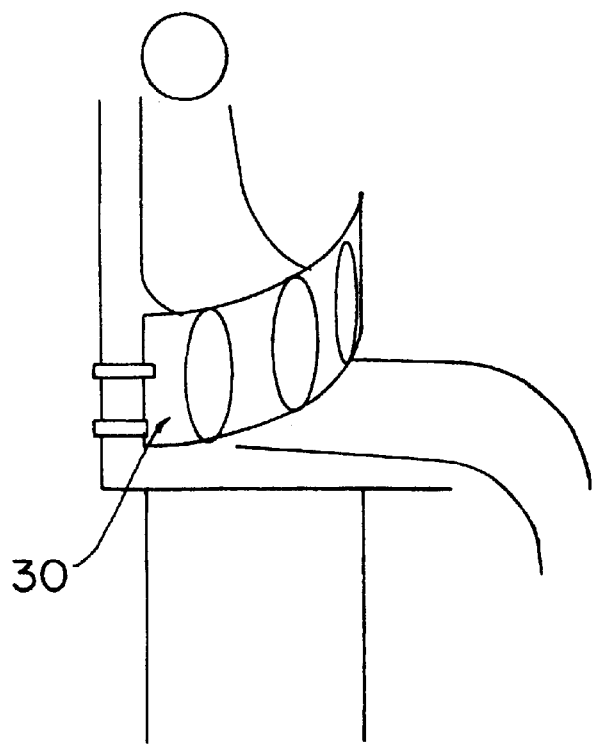
FIG. 7 is a schematic perspective view of a hinged multiphased stimulator designed to conform around the torso of the patient.

FIG. 7 suggests yet another alternative embodiment suitable for the stimulation of abdominal muscles. Here the stimulator 30 is hinged to a chair into which the patient sits. The stimulator then folds around the patient's abdomen during treatment. The stimulator 30 is again constructed of laminated permeable material having a high magnetic field saturation. Multiple windings are laid in recesses or slots which are cut into the core. The windings are designed to drive flux into the abdomen and cause a contraction of the abdominal wall muscle group. Again the windings can be phased to cause a directional massaging of this muscle group.

Having described this invention with regard to certain specific embodiments, it is to be understood that the description is not meant as a limitation since further modifications may now suggest themselves to those skilled in the art and it is intended to cover such modifications as fall within the scope of the appended claims.

We claim:

1. An apparatus comprising:
   a magnetic nerve stimulator comprising a seat; and two C-shaped cores in proximity to one another to form a common leg portion, said cores being located beneath said seat,
   wherein said magnetic nerve stimulator directs a magnetic field into the anatomy of the user when the user is sitting on said seat and stimulates nerves of the user.

2. An apparatus as claimed in claim 1, wherein said cores of said magnetic nerve stimulator are adapted to stimulate nerves which cause contraction of the bladder muscles of the user.

3. An apparatus as claimed in claim 1, wherein said magnetic nerve stimulator comprises a core of magnetic material.

4. An apparatus as claimed in claim 3, wherein said core is located beneath said seat.

5. An apparatus as claimed in claim 1, wherein said magnetic nerve stimulator comprises a core of highly saturable magnetic material, said highly saturable magnetic material comprising a magnetizable material which saturates at magnetic fields of at least 1.5 Tesla.

6. An apparatus as claimed in claim 1, wherein said magnetic nerve stimulator comprises a core of highly saturable magnetic material, said highly saturable magnetic material comprising a magnetizable material which saturates at magnetic fields of at least 2.0 Tesla.

7. An apparatus as claimed in claim 1, wherein said seat is part of a chair.

8. An apparatus as claimed in claim 3, wherein said magnetic nerve stimulator comprises a stimulator coil for carrying electrical current in proximity to said core, and electric current means connected to said stimulator coil to create an electrical current flow in said stimulator coil and cause said stimulator coil and said core to generate a magnetic field.

9. An apparatus as claimed in claim 3, wherein said magnetic material comprises a silicon steel.

10. An apparatus as claimed in claim 3, wherein said magnetic material comprises 3% grain oriented silicon steel.

11. An apparatus as claimed in claim 9, wherein said silicon steel is wound on a bobbin.

12. An apparatus as claimed in claim 9, wherein said silicon steel comprises magnetic grains, and wherein said magnetic grains are oriented azimuthally in the direction that said magnetic field will travel.

13. An apparatus as claimed in claim 3, wherein said magnetic material comprises a metallic glass.

14. An apparatus as claimed in claim 13, wherein said metallic glass is transverse field annealed.

15. An apparatus as claimed in claim 3, wherein said magnetic material comprises orthinol.

16. An apparatus as claimed in claim 3, wherein said magnetic material comprises permalloy.

17. An apparatus as claimed in claim 3, wherein said magnetic material comprises vanadium permendur.

18. An apparatus as claimed in claim 3, wherein said magnetic material comprises powdered iron.

19. An apparatus as claimed in claim 3, wherein said magnetic material comprises supermalloy.

20. An apparatus as claimed in claim 3, wherein said magnetic material comprises ferrite.

21. An apparatus as claimed in claim 1, wherein said magnetic nerve stimulator comprises:
   (a) an open core;
   (b) a stimulator coil for carrying electrical current in proximity to said core; and,
   (c) electric current means connected to said stimulator coil to create an electrical current flow in said stimulator coil and cause said stimulator coil and said core to generate a magnetic field.

22. An apparatus as claimed in claim 1, wherein said magnetic nerve stimulator comprises:

(a) an open core of highly saturable magnetic material, said highly saturable magnetic material comprising a magnetizable material which saturates at magnetic fields of at least 1.5 Tesla;

(b) a stimulator coil for carrying electrical current in proximity to said core; and, (c) electric current means connected to said stimulator coil to create an electrical current flow in said stimulator coil and cause said stimulator coil and said core to generate a magnetic field.

23. An apparatus as claimed in claim 1, wherein said magnetic nerve stimulator comprises:

(a) an open core of highly saturable magnetic material, said highly saturable magnetic material comprising a magnetizable material which saturates at magnetic fields of at least 2.0 Tesla;

(b) a stimulator coil for carrying electrical current in proximity to said core; and, (c) electric current means connected to said stimulator coil to create an electrical current flow in said stimulator coil and cause said stimulator coil and said core to generate a magnetic field.

24. An apparatus as claimed in claim 21, wherein said open core spans an angle of approximately 180 to 270 degrees.

25. An apparatus as claimed in claim 21, wherein said open core spans an angle of approximately 190 to 230 degrees.

26. An apparatus as claimed in claim 21, wherein said open core spans an angle of approximately 205 to 220 degrees.

27. An apparatus as claimed in claim 22, wherein said open core spans an angle of approximately 180 to 270 degrees.

28. An apparatus as claimed in claim 22, wherein said open core spans an angle of approximately 190 to 230 degrees.

29. An apparatus as claimed in claim 22, wherein said open core spans an angle of approximately 205 to 220 degrees.

30. An apparatus as claimed in claim 23, wherein said open core spans an angle of approximately 210 to 270 degrees.

31. An apparatus as claimed in claim 23, wherein said open core spans an angle of approximately 190 to 230 degrees.

32. An apparatus as claimed in claim 23, wherein said open core spans an angle of approximately 205 to 220 degrees.

33. As apparatus as claimed in claim 3, wherein said core has cut ends and said seat has a lower side, and wherein said cut ends are flush with said lower side.

34. An apparatus as claimed in claim 1, wherein said cores of said magnetic nerve stimulator are adapted to direct said magnetic field into the vaginal cavity of a female user.

\* \* \* \* \*